United States Patent [19]

Evans

[11] Patent Number: 4,786,639
[45] Date of Patent: Nov. 22, 1988

[54] METHOD FOR THE TREATMENT OF REVERSIBLE AIRWAYS OBSTRUCTION AND ASTHMA

[75] Inventor: John M. Evans, Roydon, England

[73] Assignee: Beecham Group p.l.c., England

[21] Appl. No.: 926,660

[22] Filed: Nov. 4, 1986

Related U.S. Application Data

[63] Continuation of Ser. No. 760,825, Jul. 31, 1985, abandoned.

[30] Foreign Application Priority Data

Jul. 31, 1984 [GB] United Kingdom ............... 8419515

[51] Int. Cl.$^4$ ............... A61K 31/50; A61K 31/495; A61K 31/53; A61K 31/47; A61K 31/445; A61K 31/44; A61K 31/41; A61K 31/425; A61K 31/42; A61K 31/415; A61K 31/40; A61K 31/35

[52] U.S. Cl. ............... 514/254; 514/241; 514/242; 514/253; 514/311; 514/312; 514/313; 514/314; 514/307; 514/309; 514/310; 514/320; 514/337; 514/362; 514/363; 514/365; 514/369; 514/370; 514/372; 514/374; 514/376; 514/377; 514/378; 514/380; 514/397; 514/403; 514/414; 514/422; 514/454; 514/455; 514/456

[58] Field of Search ............... 514/424, 320, 456, 321, 514/254, 241, 242, 253, 311–314, 307, 309, 310, 337, 362, 363, 365, 369, 370, 372, 374, 376, 377, 378, 380, 397, 403, 414, 422, 454, 455

[56] References Cited

U.S. PATENT DOCUMENTS

| 4,446,113 | 5/1984 | Evans et al. | 514/320 |
| 4,481,214 | 11/1984 | Evans | 514/456 |
| 4,496,565 | 1/1985 | Evans et al. | 514/228 |
| 4,510,152 | 4/1985 | Faruk | 514/321 |
| 4,542,149 | 9/1985 | Evans et al. | 514/320 |
| 4,555,509 | 11/1985 | Evans et al. | 514/278 |
| 4,571,406 | 2/1986 | Evans et al. | 514/274 |
| 4,575,511 | 3/1986 | Evans et al. | 514/456 |
| 4,610,992 | 9/1986 | Evans et al. | 514/320 |

Primary Examiner—Albert T. Meyers
Assistant Examiner—Freda Krosnick
Attorney, Agent, or Firm—Jacobs & Jacobs

[57] ABSTRACT

A method for the treatment and/or prophylaxis of reversible airways obstruction and asthma in mammals, which method comprises administering to the mammal in need of said treatment an effective amount of a compound of formula (I):

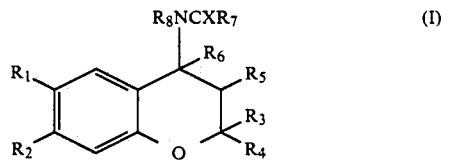

wherein $R_1$–$R_8$ and X are as set forth herein.

10 Claims, No Drawings

METHOD FOR THE TREATMENT OF REVERSIBLE AIRWAYS OBSTRUCTION AND ASTHMA

CROSS-REFERENCE

This is a continuation of Ser. No. 760,825, filed July 31, 1985, now abandoned.

The present invention relates to a method for the treatment and/or prophylaxis of disorders associated with smooth muscle contraction.

European Patent Publication Nos. 76075, 91748, 93535, 95316, 107423, 120426, 120427, 126311, 126350, 126367 and 138134 describe classes of chromanols, chromenes and chromans having anti-hypertensive activity.

It has now been discovered that compounds of this type have a mechanism of action which indicates that they are of potential use in the treatment of disorders associated with smooth muscle contraction of the gastro-intestinal tract and/or the respiratory system and/or uterus. Such disorders include peptic ulcers, irritable bowel syndrome and diverticular disease; reversible airways obstruction and asthma; and premature labour.

Accordingly, the present invention provides a method for the treatment and/or prophylaxis of disorders of the gastro-intestinal tract and/or respiratory system and/or uterus in mammals, such as humans, which method comprises administering to the mammal in need of such treatment and/or prophylaxis an effective and/or prophylactic amount of a compound of formula (I):

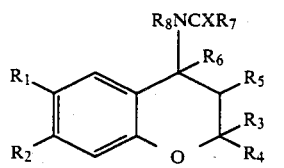

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxyethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino $C_{1-6}$ alkoxysulphinylamino or $C_{1-6}$ alkoxysulphonylamino or ethylenyl terminally substituted by $C_{1-6}$ alkylcarbonyl, nitro or cyano, or —C($C_{1-6}$ alkyl)-NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;

one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

$R_7$ is hydrogen, $C_{1-6}$ alkyl optionally substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl;aryl or heteroaryl either being optionally substituted by one or more groups or atoms selected from the class of $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl groups;

$R_8$ is hydrogen or $C_{1-6}$ alkyl; or $R_7$ and $R_8$ are joined together to form $C_{3-4}$ polymethylene or —CH$_2$—(CH$_2$)$_n$—Z—(CH$_2$)$_m$— where m and n are integers 0 to 2 such that m+n is 1 or 2 and Z is oxygen, sulphur or NR$_9$ wherein $R_9$ is hydrogen,$C_{1-9}$ alkyl, $C_{2-7}$ alkanoyl, phenyl $C_{1-4}$ alkyl, naphthylcarbonyl, phenylcarbonyl or benzylcarbonyl optionally substituted in the phenyl or naphthyl ring by one or two $C_{1-6}$ alkyl, $C_{1-6}$ alkoxy or halogen; mono-or bi-cyclic heteroarylcarbonyl;

X is oxygen or sulphur; and the $R_8$NCXR$_7$ moiety is trans to the $R_5$ group when $R_5$ is hydroxy, $C_{1-6}$ alkoxy or $C_{1-7}$ acyloxy; or a pharmaceutically acceptable salt or solvate thereof.

When one of $R_1$ and $R_2$ is hydrogen, the other is, preferably, selected from the class of halo, $C_{1-6}$ alkylcarbonyl, $C_{1-6}$ alkoxycarbonyl, nitro or cyano. In particular, when one of $R_1$ and $R_2$ is hydrogen, the other is, preferably, acetyl, chloro, nitro or cyano, especially nitro, cyano or chloro.

When one of $R_1$ and $R_2$ is hydrogen, it is preferred that $R_2$ is hydrogen.

When one of $R_1$ and $R_2$ is nitro, cyano or $C_{1-3}$ alkylcarbonyl the other is, preferably, amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano, and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing groups for $R_1$ or $R_2$ are, preferably, methyl or ethyl.

Preferably, $R_3$ and $R_4$ are both $C_{1-4}$ alkyl, in particular both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy or benzoyloxy. However, it is preferred that $R_5$ and $R_6$ together are a bond, or $R_5$ and $R_6$ are both hydrogen, or, in particular, that $R_5$ is hydroxy and $R_6$ is hydrogen.

Suitable values for $R_8$, when $R_7$ and $R_8$ are not joined together include hydrogen, methyl, ethyl, n- and iso-propyl, n-, sec- and tert-butyl. Favourably, $R_8$ is hydrogen or methyl, most preferably hydrogen.

Suitable values for $R_7$ then include hydrogen, methyl, ethyl, n- and iso-propyl, n-, sec- and tert-butyl, methyl or ethyl substituted by carboxy or chloro, vinyl,prop-1-enyl, prop-2-enyl, 1-methylvinyl, but-1-enyl, but-2-enyl, but-3-enyl, 1-methylenepropyl, 1-methylprop-1-enyl, 1-methylprop-2- enyl, (in their E and Z forms where stereoisomerism exists), and methyl or ethyl terminally substituted by hydroxy or methoxy. Favourably $R_7$ is methyl, ethyl, n- or iso-propyl of vinyl, in particular, methyl, hydroxymethyl and methoxymethyl. Preferably $R_7$ is methyl.

Examples of $R_7$ aryl include phenyl and naphthyl of which phenyl is preferred.

A sub-class of $R_7$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different.

Examples of 5- or 6-membered monocyclic heteroaryl containing one, two or three heteroatoms which are selected from the class of oxygen, nitrogen and sulphur include furanyl, thiophenyl, pyrryl, oxazolyl, thiazolyl, imidazolyl and thiadiazolyl, and pyridinyl, pyridazinyl, pyrimidinyl, pyrazinyl and triazinyl. Preferred examples of such groups include furanyl, thiophenyl, pyrryl and pyridyl, in particular 2- and 3-furanyl, 2- and 3-pyrryl, 2- and 3-thiophenyl, and 2-, 3- and 4-pyridinyl.

Examples of 9- or 10-membered bicyclic heteroaryl containing one, two or three heteroatoms which are selected from the class of oxygen, nitrogen and sulphur include benzofuranyl, benzothiophenyl, indolyl and indazolyl, quinolinyl and isoquinolinyl, and quinazoninyl. Preferred examples of such groups OS include 2- and 3-benzofuranyl, 2- and 3-benzothiophenyl, and 2- and 3-indolyl, and 2- and 3-quinolinyl.

Preferably, the number of groups or atoms for optional substitution of aryl or heteroaryl is one, two, three or four.

Preferred examples of the groups or atoms for optional substitution or aryl or heteroaryl include methyl, methoxy, hydroxy, chloro, nitro or cyano.

When $R_7$ and $R_8$ are joined together they are preferably $C_4$ or $C_5$ polymethylene or $-CH_2-(CH_2)_{n^1}-Z-(CH_2)_{m^1}-$ where $n^1$ is 0 or 1 and $m^1$ is 0 or 1.

X is preferably oxygen.

There is a favourable group of compounds within formula (I) of formula (II):

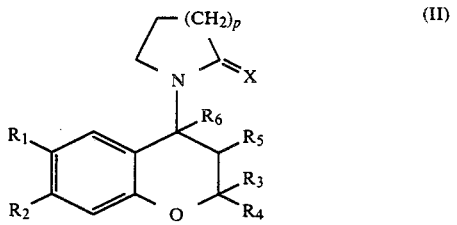

(II)

wherein p is 1 or 2 and the remaining variables are as defined in formula (I).

Examples of a pharmaceutically acceptable salt of a compound of formula (I) include the acid addition salts of a compound of formula (I), wherein one or other of $R_1$ and $R_2$ is amino or an amino-containing group, for example the hydrochloride and hydrobromide salts.

Examples of a pharmaceutically acceptable solvate of a compound of formula (I) include the hydrate.

Preferably, a compound of formula (I) is in substantially pure form.

Examples of the compounds of formula (I) include the examples desribed in the aforementioned European Patent Publications.

The compounds of formula (I), wherein $R_5$ is hydrogen, hydroxy, $C_{1-6}$ alkoxy or $C_{1-7}$ acyloxy and $R_6$ is hydrogen, are asymmetric and, therefore, can exist in the form of optical isomers. The present invention extends to all such isomers individually and as mixtures, such as racemic modifications.

The compounds of formula (I) may be prepared as described in the aforementioned European Publications, in U.S. Pat. Nos. 4,446,113, 4,481,214, 4,496,565 and 4,510,152 and allowed U.S. Ser. Nos. 482628 and 592117 (the subject matter of which are all incorporated herein by reference), or by analogous methods thereto.

The administration of a compound of formula (I) or a pharmaceutically acceptable salt thereof may be by way of oral administration or parenteral administration, or (for asthma) in a spray, aerosol or other conventional method for inhalation.

An amount effective to treat the disorders hereinbefore described depends on the usual factors such as the nature and severity of the disorders being treated and the weight of the mammal. However, a unit dose will normally contain 0.1 to 50 mg for example 0.5 to 10 mg, of the compound of formula (I) or a pharmaceutically acceptable salt thereof. Unit doses will normally be administered once or more than once a day, for example 2, 3, or 4 times a day, more usually 1 to 3 times a day, such that the total daily dose is normally in the range, for a 70 kg adult of 0.1 to 50 mg, for example 0.5 to 10 mg, that is in the range of approximately 0.001 to 1 mg/kg/day, more usually 0.005 to 0.2 mg/kg/day.

No adverse toxicological effects are indicated at the aforementioned dosage ranges.

It is greatly preferred that the Compound of formula (I) or a pharmaceutically acceptable salt thereof is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention also provides the use of a compound of formula (I) or a pharmaceutically acceptable salt thereof for the manufacture of a medicament for the treatment and/or prophylaxis of disorders of the gastro-intestinal tract and/or respiratory system and/or uterus. Such treatment and/or prophylaxis may be carried out as hereinbefore described.

The present invention further provides a pharmaceutical composition for use in the treatment and/or prophylaxis of disorders of the gastro-intestinal tract and/or respiratory system and/or uterus which comprises a compound of formula (I) or a pharmaceutically acceptable salt thereof and a pharmaceutically acceptable carrier.

Such compositions may be prepared in the manner as hereinbefore described.

The following pharmacological data illustrate the activity of compounds of formula (I) in tests which are indicative of compounds of potential use in the treatment of disorders of the gastro-intestinal tract, respiratory system and uterus.

N.B. Compound 1 is 6-cyano-3,4-dihydro-2,2-dimethyl-trans-4-(2-oxo-1-pyrrolidinyl)-2H-benzo[b]pyran-3-ol and compound 2 is 6-chloro-3,4-dihydro-2,2-dimethyl-trans-4-(2-oxo-1-pyrrolidinyl)-2H-benzo[b]pyran-3-ol (compounds of examples 1 and 12, respectively, of U.S. Pat. No. 4,446,113). Compound 3 is trans-4-(N-acetyl)-methylamino-6-cyano-3,4-dihydro-2,2-dimethyl-2H-benzo[b]pyran-3-ol and compound 4 is trans-4-(N-acetyl)-ethylamino-6-cyano-3,4-dihydro-2,2-dimethyl-2H-benzo[b]pyran-3-ol (compounds of examples 5 and 1, respectively, of U.S. Pat. No. 4,481,214).

BIOLOGICAL DATA

Methods (1) Rat isolated portal vein. Male Sprague Dawley rats (250–350 g) were killed by cervical dislocation. Portal veins (2–3cm in length) were set up under 0.8–1 g tension in a 10 ml organ bath containing Krebs-Henseleit solution, at 37° C., of the following composition (mM): NaCl 118, NaHCO$_3$ 25, glucose 5, KH$_2$PO$_4$ 1.18, KCl 4.69, MgSO$_4$ 0.59, CaCl$_2$.H$_2$O 1.87. The tissue was aerated with a 95% oxygen and 5% carbon dioxide mixture. Isometric tension was recorded using a Devices strain gauge and recorder. Each preparation was allowed 1h to equilibrate before the addition of test compound. The ability of a compound to inhibit the contractions due to added calcium (3 mM CaCl$_2$) was determined in tissues bathed in Krebs-Henseleit solution containing 0.05 mM CaCl$_2$ (in order to reduce spontaneous contractions). Then percentage inhibition (mean $\pm$s.e.m.; 6–9 tissues) of the amplitude of the spontaneous contractions, and contractions due to added calcium, was determined after 15 min contact time with test compound.

(2) Rabbit isolated mesenteric artery. Mesenteric arteries (3 mm rings) were removed from male New Zealand White rabbits and mounted, at a resting tension of 1.5–2.0 g, in a 10 ml organ bath containing a Ringer solution, at 37° C., of the following composition (mM): NaCl 120.8; KCl 5.9; CaCl$_2$ 2.5; MgCl$_2$ 1.2; HEPES 5.8; glucose 11.5. The bathing solution was bubbled with a 95% oxygen and 5% carbon dioxide mixture. Each preparation was allowed 1–1½ h to equilibrate before the addition of either 30 or 90 mM KCl to contract the tissue. The ability of test compound to relax the sustained contraction due to KCl was determined by assessing the % reduction (mean $\pm$s.e.m.; 4–9 tissues) produced by varying concentrations of test compound.

RESULTS (1) Rat Isolated Portal Vein: effect of compound 1 on spontaneous contractions and those due to added calcium.

|  | IC$_{50}$ × 10$^{-7}$ M | |
| --- | --- | --- |
|  | Spontaneous | Ca$^{2+}$ (3 mM) |
| Compound 1 | 1.2 | 1.5 |
|  | (0.67–7.8) | (0.87–3.5) |

IC$_{50}$ is concentration of compound reducing contractions by 50%; parenthesis indicate 95% fiducial limits.

Thus, compound 1 is equipotent as an inhibitor of spontaneous contractions and of those due to added calcium in this isolated blood vessel preparation.

(2) Rabbit Isolated Mesenteric Artery: effect of compound 1 on contractions due to 30 and 90 mM KCl.

|  | IC$_{50}$ × 10$^{-7}$ M | |
| --- | --- | --- |
|  | 30 mM KCl | 90 mM KCl |
| Compound 1 | 5.1 | >10$^{-5}$ M |
|  | (1.5–18) |  |

IC$_{50}$ is the concentration of compound 1 halving the contraction due to KCl; parenthesis indicate 95% fiducial limits.

Thus, compound 1 antagonises the contractions due to a partially, but not a fully, depolarising concentration of potassium. The effect of compound 1 on contractions mediated by a low concentration of KCl is consistent with the compound hyperpolarising the membrane potential and thereby rendering the potential operated calcium channels less able to open in response to a depolarising stimulus; by this mechanism calcium influx is reduced.

The effectiveness of compound 1 against a high concentration of KCl indicates that the marked depolarisation due to KCl overcomes the hyperpolarising action of compound 1.

Compounds of the examples described in the aforementioned European Publications, European Patent Applications and U.S. patent may also be tested and found to be active in tests 1 and 2.

PHARMACOLOGICAL DATA

1. Gastro-Intestinal Tract.

Rat isolated colon. Male Wister rats (Charles River U.K.) were killed by a blow on the head and a 2 cm segment of proximal colon excised. After gently washing free any luminal contents the tissue was suspended longitudinally in a 10 ml organ bath containing Krebs solution of the following composition: NaCl 118.1 mM, $KH_2PO_4$ 1.18 mM, $NaHCO_3$ 25 mM, KCl 4.69 mM, $MgSO_4$ 1.64 mM, $CaCl_2$ 2.52 mM, Glucose 11.1 mM. This solution was maintained at 37° C. and constantly bubbled with 95% $O_2$: 5% $CO_2$. Isometric contractions were recorded from the tissue with an initial tension of 1 g being applied.

The inhibitory effects of compounds 1+2 were assessed from the reduction in amplitude of the spontaneous contractions of the colon. Cumulative dose-response curves were constructed with the compounds being applied to the bath at intervals of 10 mins. $ID_{50}$ (concentration of drug reducing amplitude of contractions by 50%) was graphically determined from the dose-response curve.

Rat isolated colon : effect of compounds 1 and 2 on spontaneous contractions

|  | $ID_{50}$ μg/ml |
| --- | --- |
| Compound 1 | 0.12 |
| Compound 2 | 1.7 |

2. Respiratory Tract a. Guinea Pig Lung Strip Screen

This model of smooth muscle relaxation of isolated peripheral guinea pig airways is based on the method of Lulich et al [Clin. Exp. Pharm. Phys. 6, 625-629 (1979)].

Two parenctymal lung strips were prepared, one from each caudal lobe, by cutting a strip approximately 3 mm wide from the outer periphery of each lobe. The preparations were mounted in 10 ml organ baths filled with krebs solution at 37° C. and bubbled with 5% $CO_2$ in $O_2$. Changes in isometric muscle tension were monitored and a resting tension of 2 g was applied to the tissues which were allowed to equilibrate for 60 min. During the equilibration period the tissues were washed at 15 min. intervals and the resting tension readjusted to 2 g if necessary.

Following equilibration, the lung strips were given a submaximal dose of histamine ($2 \times 10^{-6}$ m) to confirm the sensitivity of the preparations. The tissues were then dosed cumulatively with histamine ($10^{-9}$ m–$10^{-4}$ m) accordingly to the method of Van Rossum [Arch.Int. Pharmacodyn.Ther. 143, 299—(1963)]. After washing and re-equilibration the tissues were exposed to the test compound ($10^{-5}$ m) for 20 min. prior to constructing a second, cumulative concentration-contraction response to histamine. Appropriate dose-response curves to histamine in the absence, and in the presence, of test compound were drawn and the effects of the test compound on the threshold dose and $ED_{50}$ of histamine were noted; the effect on the maximal histamine response was also determined. Inhibition of the histamine-induced contraction may be reflected by an increase in threshold concentration, an increase in $ED_{50}$ value or a decrease in the maximum response elicited by histamine.

b. Guinea Pig Asphyxic Collapse Model in-vivo

This model is based on the method described by Herxheimer (Br.J.Pharm.50, 314 (1974)]. Conscious female guinea pigs (Dunkin-Hartley strain, 500-700 g body weight) were placed individually into a Perspex chamber of approximately 8 litres capacity, and the animals were challenged with an histamine aerosol. The standard histamine aerosol was generated using a Monaghan 675 ultrasonic nebulizer (power setting 7) from a $5 \times 10^{-5}$ m solution of histamine acid phosphate in distilled water. After obtaining satisfactory aerosol generation, the aerosol was passed into the chamber for 10 seconds and the time was recorded from introduction of the aerosol until the guinea pig collapsed (termed asphyxic collapse). The animal was rapidly removed and allowed to recover. In this way, the mean time to asphyxic collapse for a group of guinea pigs was determined.

Compounds were administered orally to groups of animals and the degree of protection against histamine-induced asphyxic collapse was determined by the percentage increase in mean time to asphyxic collapse of a compound-treated group to asphyxic collapse for control groups was around 80–100 seconds. Compound-treated animals that did not collapse were considered to be 100% protected.

Compounds were administered in 1% methyl cellulose at a concentration of 5 mg/kg (1 ml/kg body weight) and the animals were challenged with the standard histamine aerosol after 30 min.

The significance of any increase in the mean asphyxic collapse time of a compound-treated group of animals over that of a vehicle-treated control group was determined using students "t" test.

The results were as follows:

(a) GUINEA-PIG ISOLATED LUNG STRIP: antagonism of histamine contractions. Each compound tested at $10^{-5}$ M.

| N | Compound | Threshold conc. for histamine | Conc. of hist. for 50% max. contraction |
| --- | --- | --- | --- |
| 6 | 1 | $8.5 \times 10^{-7}$ | $2.2 \times 10^{-5}$ |
|  |  | $\pm 1.5 \times 10^{-7}$ | $\pm 1.4 \times 10^{-5}$ |
|  | CONTROL | $1 \times 10^{-7}$ | $1.9 \times 10^{-6}$ |
|  |  | $\pm 0.4 \times 10^{-7}$ | $\pm 0.3 \times 10^{-6}$ |
| 6 | 3 | $1 \times 10^{-6}$ | $7.8 \times 10^{-6}$ |
|  |  |  | $\pm 3.3 \times 10^{-6}$ |
|  | CONTROL | $1.7 \times 10^{-7}$ | $3 \times 10^{-6}$ |
|  |  | $\pm 1.2 \times 10^{-7}$ | $\pm 0.7 \times 10^{-6}$ |

Neither compound affected the maximum response to histamine.

(b) CONSCIOUS GUINEA-PIG

Histamine collapse (aerosol administration) Test compound 30 minutes pretreatment.

| Compound | Dose (p.o.) | N | Mean collapse time (sec) |
| --- | --- | --- | --- |
| 1 | 5 mg/kg | 5 | 154 ± 26* |
| 4 | 5 mg/kg | 4 | 176 ± 25** |
| CONTROL | | 6 | 90 ± 10 |

*$p < 0.05$;
**$p < 0.01$.

3. Uterus

Relaxation of Potassium Depolarised Rat Uterus

Female Sprague Dawley rats (120–160 g) were sacrificed and the uterine horns removed. Each horn was cut longitudinally to give a sheet of muscle which was further subdivided to give two preparations (i.e. 4 from each animal). Each tissue was mounted in a 10 ml organ bath containing normal Krebs buffer at 32° C. and gassed with 95% $O_2$-5% $CO_2$. During an equilibration period of approximately 45 min the tissues were repeatedly stretched and washed to maintain a resting tension of 0.2 g. An increase in tension was induced by exchanging the Krebs buffer for one in which the sodium ions were replaced by the equivalent amount of potassium ions.

This caused the tissues to contract followed by a slow relaxation which equilibrated at a level above the initial resting level. A cumulative concentration effect curve to compound 1 was then carried out until the response to the final bath concentration ($10^{-4}$M) had stabilised. Incremental concentrations of isoprenaline were then added until the tissues had fully relaxed. Results are expressed as a percentage of this maximum relaxation.

RESULTS

| Compound 1 | % maximum relaxation |
| --- | --- |
| $3 \times 10^{-6}$ M | 6 ± 2 |
| $1 \times 10^{-5}$ M | 18 ± 3 |
| $3 \times 10^{-5}$ M | 31 ± 3 |
| $1 \times 10^{-4}$ M | 61 ± 6 |

7 preparations were used.

I claim:

1. A method for the treatment of reversible airways obstruction, in mammals, which method comprises administering to a mammal in need of such treatment an effective amount of a compound of formula (I):

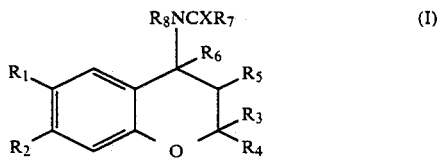

wherein:
either one of $R_1$ or $R_2$ is hydrogen and the other is $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, $C_{1-6}$ alkyl-thiolmethyl, formyl, aminosulphinyl, aminosulphonyl or aminocarbonyl, the amino moiety being unsubstituted or substituted by one or two $C_{1-6}$ alkyl groups, or $C_{1-6}$ alkylsulphinylamino, $C_{1-6}$ alkylsulphonylamino, $C_{1-6}$ alkoxysulphinylamino, $C_{1-6}$ alkoxysulphonylamino or ethylenyl terminally substituted by $C_{1-6}$ alkylcarbonyl, nitro, cyano, —C($C_{1-6}$ alkyl) NOH or —C($C_{1-6}$ alkyl)NNH$_2$, or either one of $R_1$ or $R_2$ is nitro, cyano or $C_{1-3}$ alkylcarbonyl and the other is methoxy or amino unsubstituted or substituted by one or two $C_{1-6}$ alkyl or by $C_{2-7}$ alkanoyl; either one of $R_3$ or $R_4$ is hydrogen or $C_{1-4}$ alkyl and the other is $C_{1-4}$ alkyl or $R_3$ and $R_4$ together are $C_{2-5}$ polymethylene; $R_5$ is hydrogen, hydroxy, $C_{1-6}$ alkoxy or $C_{1-7}$ acyloxy and $R_6$ is hydrogen, or $R_5$ and $R_6$ together are a bond; $R_7$ is hydrogen, $C_{1-6}$ alkyl unsubstituted or substituted by hydroxy, $C_{1-6}$ alkoxy, $C_{1-6}$ alkoxycarbonyl or carboxy, $C_{1-6}$ alkyl substituted by halogen, or $C_{2-6}$ alkenyl, phenyl, naphthyl or heteroaryl each of which is unsubstituted or substituted by $C_{1-6}$ alkoxy, hydroxyl, halogen, trifluoromethyl, nitro, cyano, $C_{1-12}$ carboxylic acyl or amino or aminocarbonyl unsubstituted or substituted by one or two $C_{1-6}$ alkyl groups and wherein the heteroaryl moiety is selected from the list of groups as defined hereinafter;

$R_8$ is hydrogen or $C_{1-6}$ alkyl; or $R_7$ and $R_8$ are joined together to form $C_{3-4}$ polymethylene or —CH$_2$—(CH$_2$)$_n$—Z—(CH$_2$)m— where m and n are integers of 0 to 2 such that m+n is 1 or 2 and z is oxygen, sulphur or NR$_9$ wherein R$_9$ is hydrogen, $C_{1-9}$ alkyl, $C_{2-7}$ alkanoyl, phenyl $C_{1-4}$ alkyl, naphthylcarbonyl, phenylcarbonyl or benzylcarbonyl unsubstituted or substituted in the phenyl or naphthyl ring by one or two $C_{1-6}$ alkyl, $C_{1-6}$ alkoxy or halogen; heteroaryl carbonyl; and wherein heteroaryl moieties in $R_7$ and $R_9$ are selected from the group consisting of furanyl, thiophenyl, pyrryl, oxazolyl, thiazolyl, imidazolyl, thiadiazolyl, pyridinyl, pyridazinyl, pyrimidinyl, pyrazinyl, triazinyl, benzofuranyl, benzothiophenyl, indolyl, indazolyl, quinolinyl, isoquinolinyl and quinazoninyl;

X is oxygen or sulphur; and the $R_8$NCXR$_7$ moiety is trans to the $R_5$ group when $R_5$ is hydroxy, $C_{1-6}$ alkoxy or $C_{1-7}$ acyloxy; or a pharmaceutically acceptable salt or hydrate thereof.

2. A method according to claim 1 wherein either one of $R_1$ and $R_2$ is hydrogen and the other is chloro, $C_{1-6}$ alkylcarbonyl, $C_{1-6}$ alkoxycarbonyl, nitro or cyano.

3. A method according to claim 2 wherein $R_1$ is cyano or chloro and $R_2$ is hydrogen.

4. A method according to claim 1 wherein $R_3$ and $R_4$ are both methyl.

5. A method according to claim 1 wherein $R_5$ is hydroxy and $R_6$ is hydrogen.

6. A method according to claim 1 wherein $R_7$ and $R_8$ are joined to form $C_3$ or $C_4$ polymethylene.

7. A method according to claim 1 wherein $R_7$ is methyl and $R_8$ is methyl, ethyl or hydrogen.

8. A method according to claim 1 wherein the compound of formula (I) is of formula (II):

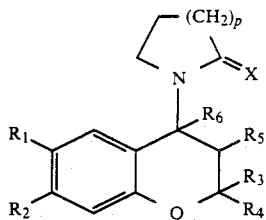

(II)

wherein p is 1 or 2 and the remaining variables are as defined in claim 1.

9. A method according to claim 1 wherein the compound of formula (I) is 6-cyano-3,4-dihydro-2,2-dimethyl-trans-4-(2-oxo-1-pyrrolidinyl)-2H-benzo[b]pyran-3-ol;6-chloro-3,4-dihydro-2,2-dimethyl-trans-4-(2-oxo-1-pyrrolidinyl)-2H-benzo[b]p-yran-3-ol;trans-4-(N-acetyl)-methylamino-6-cyano-3,4-dihydro-2,2-dimethyl-2H-benzo[b]pyran-3-ol or trans-4-(N-acetyl)-ethylamino-6-cyano-3,4-dihydro-2,2-dimethyl2H-benzo[b]pyran-3-ol.

10. A method for the treatment of asthma which method comprises administering an anti-asthmatic effective amount of a compound of formula I of claim 1 to a subject in need of said treatment.

* * * * *